United States Patent [19]

Burrows

[11] 4,221,130

[45] Sep. 9, 1980

[54] GAS SAMPLING DEVICE

[75] Inventor: Donald E. Burrows, Santa Barbara, Calif.

[73] Assignee: Anarad Inc., Santa Barbara, Calif.

[21] Appl. No.: 42,171

[22] Filed: May 24, 1979

[51] Int. Cl.³ .............................................. G01N 1/22
[52] U.S. Cl. ........................... 73/421.5 R; 73/422 R; 128/719
[58] Field of Search ................... 73/421.5 R, 421.5 A, 73/422 R; 128/719

[56] References Cited

U.S. PATENT DOCUMENTS

| | | | |
|---|---|---|---|
| 3,472,067 | 10/1969 | Chew | 73/421.5 R |
| 3,921,458 | 11/1975 | Logan | 73/421.5 R |
| 3,927,670 | 12/1975 | Turney et al. | 128/719 |

FOREIGN PATENT DOCUMENTS 1103522  3/1961  Fed. Rep. of Germany .

*Primary Examiner*—S. Clement Swisher
*Attorney, Agent, or Firm*—Robert M. Skolnik; William R. Evans

[57] ABSTRACT

A gas sampling device has a gas-entry passage dimensioned to provide laminar flow to the gas and opening into a larger gas-receiving passage. A gas sampling tube is supported from the larger gas-receiving passage, extends only to the smaller gas-entry passage for sampling the entering gas, and is coaxially spaced from the walls of the gas-entry passage to sample the gas in the gas-entry passage without dilution from the gas-receiving passage or interference with the gas flow. The device is particularly useful for sampling small exhaled breath gas flow in combination with neonatal respiratory apparatus for sampling the breath of neonates.

5 Claims, 1 Drawing Figure

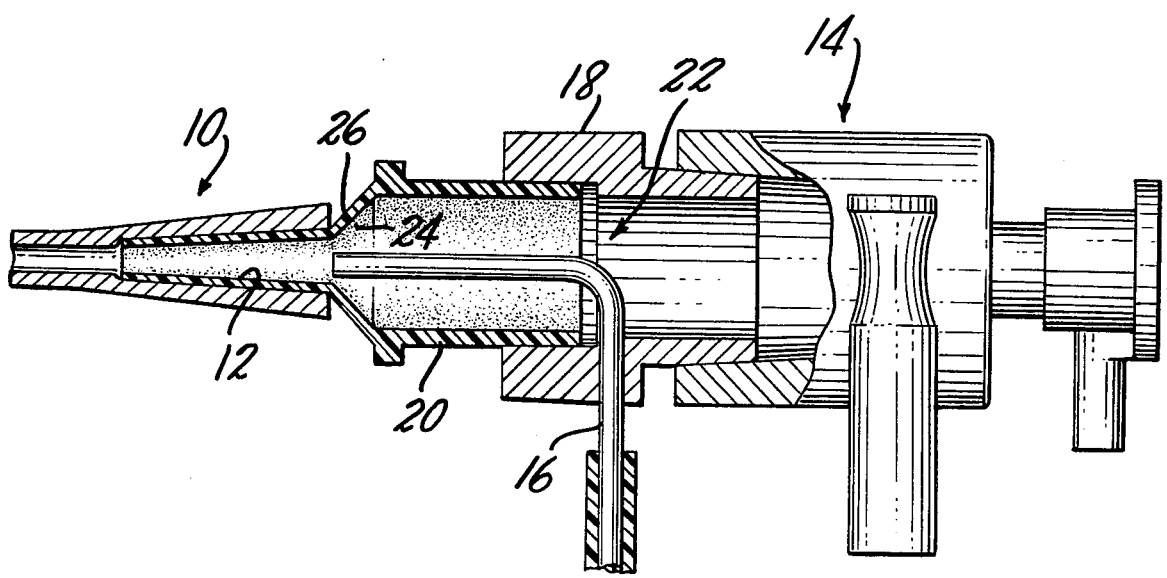

GAS SAMPLING DEVICE

BACKGROUND OF THE INVENTION

The invention relates to a device for sampling a flowing gas.

Many medical and industrial activities require samples of flowing gases for analysis and control of the activity. When the flow of such gases is very small, however, it has been difficult to provide a device which samples the gases accurately and without undesirably interfering with the limited flow of the gas.

In medical activities such as the administration of ventilation or anesthesia gases to patients with an endotracheal tube, for example, the gas exhaled by the patient can be sampled and analyzed for diagnosis or control of the apparatus. With adult patients, the endotracheal tube is large enough to accomodate a coaxial sampling tube, but with infants or neonates, the endotracheal tube is too small for such an arrangement. In addition, the flow of gas from the neonate is so small that the gas sampling apparatus can easily interfere with the flow of gas.

Typically, the necessarily small endotracheal tube for use on a neonate is connected to larger tubing more practical for administering the respiratory or anesthesia gases in a valve arrangement which also vents the gases exhaled by the neonate. Because the flow of exhaled gas is small and the valve arrangement is of relatively substantial volume to be of a practical size, the exhaled gases mix with gases supplied for the previous inhalation cycle in the valve arrangement. Sampling the exhaled gas after it leaves the endotracheal tube thus provides an inaccurate sample. It has therefore been the practice to try to position a flexible gas-sampling tube as close to the connection to the endotracheal tube as possible. The flexible tube, however, had to be about the same size as the neonatal endotracheal tube to be positionable, and thus could substantially block the endotracheal tube if it got too close. The resulting compromise in positioning the flexible tube near enough the endotracheal tube for an accurate sample but not blocking it, and the difficulty of achieving even this compromise, made the arrangement impractical.

SUMMARY OF THE INVENTION

It is therefore an object of the invention to provide a device for sampling a flowing gas, and particularly a device for accurately sampling small gas flows.

To this end, the invention provides a device having a gas-entry passage dimensioned in accordance with the gas flow for providing substantially laminar flow to the gas. The gas-entry passage opens into a larger gas-receiving passage of, for example, a size for more convenient handling. A rigid gas sampling tube is supported from the larger gas-receiving passage, projects only to the gas-entry passage, and is spaced coaxially from the walls thereof for sampling the laminar flow of the gas in the gas entry passage without interfering with the flow of the gas to be sampled even when the gas flow is very small. In addition, the laminar flow of the gas in the gas entry passage prevents mixture of the gas flow to be sampled with gases which may remain in the larger gas-receiving passage, particularly in the center of the laminar gas flow. Positioning the sampling tube coaxially of the gas-entry passage thus provides the most accurate sample of the flowing gas. A still further advantage of the spaced, coaxial position of the gas sampling tube is that condensation or other fluids from the walls of the gas-entry passage cannot flow into the sampling tube to block the tube or interfere with instruments for analyzing the sampled gas.

Each of these advantages of the invention is especially important when the flow of gas to be sampled is very small and moist as with the exhalation gas of a neonate through an endotracheal tube which is connected to a respiratory device such as a ventilator or anesthesia device by the sampling device. In this arrangement, the gas-entry passage which is small enough relative even to the limited exhalation breath gas flow to make the exhaled gases flow laminarly restricts the back-flow or dilution of the exhaled breath gas to be sampled with respiration or anesthesia gases remaining in the enlarged gas-receiving portion from the preceding inhalation cycle. Sampling the exhaled breath gas at the gas entry passage, and particularly at the center thereof, thus provides the most accurate breath sample. Positioning the sampling tube at and in the center of the gas-entry passage where it enlarges into the gas-receiving passage also avoids flow interference. Supporting the sample tube only in the larger gas receiving passage still further avoids flow interference. The arrangement also can be made in just two mating parts, one for connection to the endotracheal tube and one for connection to the respirator or anesthesia device. The sampling arrangement then also provides a convenient adapter for the differing passage dimensions of the endotracheal tube and respiratory device having a minimum of dead space which can interfere with regulating the respirator or anesthesia device.

DESCRIPTION OF THE DRAWINGS

A preferred embodiment which illustrates but does not limit the invention will now be described with reference to the FIGURE which is an enlarged elevation, partly in section, of the preferred embodiment.

DESCRIPTION OF THE PREFERRED EMBODIMENT

The preferred embodiment is a device for sampling the exhaled breath gas of a neonate. The breath gas is supplied through an endotracheal tube having a proximal end at 10 in which a gas entry passage 12 of the device is received. At the opposite end of the device is a gas supply valve arrangement 14 of a ventilator. During inhalation, gas flows from the ventilator valve at 14 to the gas-entry passage 12 and endotracheal tube at 10 and during exhalation, gas flows in the opposite direction from the endotracheal tube at 10 and the gas-entry passage 12 to the ventilator valve at 14. During exhalation, with the expired breath gas flowing into the gas entry passage 12 from the endotracheal tube at 10, or to the right in the Figure, the expired breath gas is sampled with a gas sample tube 16.

The gas sample tube is an L-shaped, rigid pipe extending from a supporting connection in one member 18 of the device to the gas-entry passage 12 which is in another member 20 of the device. The two members 18, 20 mate in gas-tight sliding engagement so that they may be separated as desired for easier connection of the endotracheal tube to the gas entry passage, or for other reasons. The end of the member 18 opposite that which mates with the gas-entry passage member 20 mates with the ventilator valve 14 and thus has the convenient, approximately one half inch (1.2 cm) flow line dimensions of such equipment and defines a larger gas-receiving passage 22 in the two mating members 18, 20.

The larger dimensions of the gas-receiving passage 22 are too big to maintain laminar flow of the limited breath exhalation gas flow from a neonate. The gas-entry passage 12, however, is dimensioned relative to the exhalation flow to establish or maintain laminar flow of the exhalation gas in the gas-entry passage. The sample tube 16 extends just to the proximal end of the gas-entry passage 12 where it opens into the gas-receiving passage 22, as shown in the Figure, to sample the laminar flow of the exhaled breath gas. The sample tube 16 is also positioned by its support on the member 18 and the mated position of the member 20 therein to be coaxially spaced from the walls of the gas entry passage. This structural arrangement provides the several gas-sampling improvements of the invention.

By positioning the gas-sampling tube where the gas-entry opens into the larger gas-receiving passage even a slight spacing of the tube from the walls of the gas-entry passage is sufficient to keep the tube from substantially limiting the gas flow. This is particularly important when the gas flow is small, because the gas-entry passage is then correspondingly small to provide the laminar flow for better sampling and the sample tube size required to obtain a sample may be so close to that of the gas entry passage as to restrict the gas flow if the sample tube projected further into the gas-entry passage. Supporting the gas-sampling tube from the larger gas receiving passage further avoids restricting the gas flow with the support, and also avoids interference with the laminar flow.

Providing the laminar flow in the gas-entry passage where the gas is sampled is important to avoid dilution of the gas to be sampled with other gases. Turbulent flow would tend to mix in some other gases from the gas-receiving passage, such as anesthesia gases from the preceeding inhalation breath cycle when the valve 14 connects to an anesthesia device, and thus provide an inaccurate sample of the exhaled gas. Positioning the gas-sampling tube centrally of the gas-entry passage also samples the central, maximum gas flow to aid the anti-dilution effect and avoids picking up moisture from the walls of the gas receiving passage. The anti-dilution effect is also heightened by providing progressively diverging walls 24 connecting the gas-entry passage 12 to the gas-receiving passage 22 to help direct a flow of gas away from the gas sample tube.

The exterior portion 26 at the diverging junction of the gas-entry passage with the larger gas-receiving passage provides a flange which locates the proximal end of the endotracheal tube 10 on the exterior of the gas-receiving passage. Predictably locating the gas-sampling tube in relation to the endotracheal tube in this way further assists in accurately sampling the gas.

The gas-receiving passage 22 is preferably only about ¾ inch (1.9 cm) long to minimize the dead space which is added to the ventilator or anesthesia system by the sampling device. Such dead-space with the pressure-elasticity of gases can interfere or at least alter the performance of the ventilator or anesthesia devices if it is excessive. The small size of the gas sampling device minimizes such effects.

Having thus described my invention,

I claim:

1. A device for sampling a flowing gas comprising:

gas-entry means defining a passage for receiving the flowing gas and providing substantially laminar flow to the gas to an exit end;

gas-receiving means of larger capacity than the passage of the gas-entry means and connected to the exit end of the gas-entry means for receiving the flowing gas from the exit end of the gas-entry means without substantial return dilution thereto; and a gas-sampling tube supported only at one end from the gas-receiving means for not impairing the laminar flow in the gas entry means and projecting at the other end only to the exit end of the gas-entry means and coaxially spaced from the passage therein for sampling the flowing gas, the gas-sampling tube projecting through the gas receiving means for connection to a device processing the sampled gas.

2. A device for sampling a flowing gas comprising:

a first member having a gas-entry passage at one end of sufficiently small diameter relative to the gas flow to establish substantially laminar flow of the gas therein and opening into a gas-receiving passage of larger diameter at the other end; and a second member having a sleeve and gas-sampling tube, the sleeve being of a diameter for mating with the gas-receiving passage, and supporting the gas-sampling tube which extends out of the sleeve for connection to a gas processing device at one end, and only to and coaxially spaced from the gas-receiving passage at the other end when the members are mated.

3. The device of claim 1 or 2 and further comprising, in combination, a respiratory device connected to the gas-receiving passage for supplying a second gas and an endotracheal tube connected to the gas-entry passage for carrying the second gas to a patient during inhalation and providing the flowing gas to be sampled during exhalation.

4. The device of claim 3 and further comprising means on the gas-entry passage for locating the proximal end of the endotracheal tube at the end of the gas-sampling tube in the gas-receiving passage.

5. The device of claim 1 or 2 and further comprising progressively diverging walls connecting the gas-entry passage to the gas-receiving passage.

* * * * *